United States Patent [19]

Gindler et al.

[11] 4,357,144

[45] Nov. 2, 1982

[54] COLORIMETRIC UREA DETERMINATION IN PRESENCE OF LONG HYDROCARBON CHAIN AMIDOBETAINE

[75] Inventors: E. Melvin Gindler, Union City; Olga Daskalakis, Burlingame, both of Calif.

[73] Assignee: Sherwood Medical Industries Inc., St. Louis, Mo.

[21] Appl. No.: 292,959

[22] Filed: Aug. 14, 1981

[51] Int. Cl.³ .................. G01N 33/52; G01N 33/62
[52] U.S. Cl. .................. 23/230 B; 23/924; 252/408; 422/61
[58] Field of Search .............. 23/230 B, 924; 422/61; 252/408

[56] References Cited

U.S. PATENT DOCUMENTS

| | | | |
|---|---|---|---|
| 4,215,995 | 8/1980 | Turk | 23/924 X |
| 4,239,649 | 12/1980 | Gindler | 23/230 B X |
| 4,273,556 | 6/1981 | Gindler | 23/230 B |

OTHER PUBLICATIONS

Chemical Abstracts, 90:199783u (1979).

*Primary Examiner*—Sidney Marantz
*Attorney, Agent, or Firm*—Wegner, McCord, Wood & Dalton

[57] ABSTRACT

A colorimetric urea determination method, reagent, and reagent kit useful in end point and kinetic urea determination. Urea in a liquid sample reacts with o-phthalaldehyde and chromotropic acid or one of its salts in the presence of a linear long hydrocarbon chain amidobetaine to produce an intensely colored reaction product, the concentration of which is linearly related to the urea concentration in the sample.

16 Claims, No Drawings

COLORIMETRIC UREA DETERMINATION IN PRESENCE OF LONG HYDROCARBON CHAIN AMIDOBETAINE

BACKGROUND OF THE INVENTION

1. Field of the Invention

This invention relates to urea assay methodology and, more particularly, this invention relates to a colorimetric urea determination method, reagent and reagent kit useful in end point and kinetic urea determination determination methods.

2. Description of the Prior Art

Gindler U.S. Pat. No. 4,273,556 (June 16, 1981), the disclosure of which is hereby incorporated by reference, describes a method of urea demonstration and determination in which urea reacts with o-phthalaldehyde and a chromogenic compound comprising chromotropic acid or one of its salts to produce an intensely colored reaction product.

According to the prior Gindler patent, o-phthalaldehyde reacts in an acidic medium with urea present in a liquid sample to form a substantially colorless isoindoline derivative, which in turn reacts with chromotropic acid, or one of its salts, to produce an intensely colored substance of unknown structure whose concentration is linearly related to urea concentration.

It has been found in practice that, while the reaction system described in the prior Gindler patent exhibits excellent precision in an end point urea determination, the precision of the kinetic method of analysis, in which absorbance readings of the reaction vessel and a calibrator are taken at two time points and the difference between the absorbances compared, is inferior to the precision of the end point method.

Further, when an aqueous calibrator is used in serum assays, an empirical conversion factor between serum absorbance and serum urea concentrations is required.

SUMMARY OF THE INVENTION

It is an object of the invention to overcome one or more of the problems described above.

According to the present invention, the colorimetric reaction between urea, o-phthalaldehyde, and chromotropic acid or one of its salts is carried out in the presence of a long hydrocarbon chain amidobetaine. Preferred amidobetaines have the following structures:

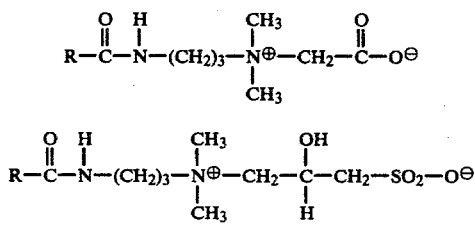

wherein R represents a straight chain coconut residue having between about 10 and 20 carbon atoms.

The amidobetaine may be used as the only surfactant in the system, and effectively prevents protein precipitation at low pH. Precision of the reaction system when used in a kinetic urea determination method is enhanced, and no empirical conversion factor between serum urea and absorbance is necessary when an aqueous calibrator is used.

Other objects and advantages of the invention will be apparent from the following detailed description taken in conjunction with the appended claims.

DETAILED DESCRIPTION OF THE INVENTION

According to the present invention, o-phthalaldehyde reacts in an acidic medium with urea present in a liquid sample to form a substantially colorless isoindoline derivative concentrate, according to the following:

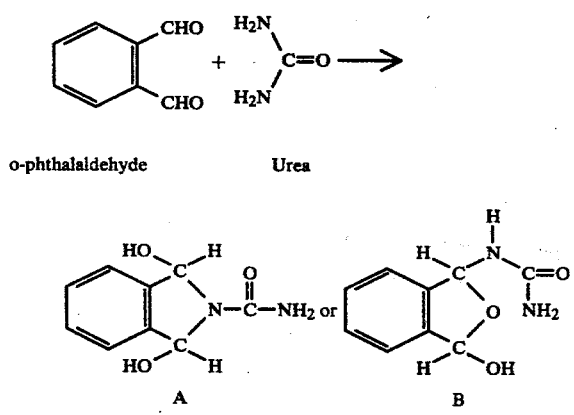

A chromogen comprising chromotropic acid or one of its salts reacts with either intermediate (form A or B) in the presence of a long chain amidobetaine to produce an intensely colored substance of unknown structure whose concentration is linearly related to urea concentration, and which follows Beer's law over a wide range of urea concentrations.

Chromotropic acid (4,5-dihydroxynaphthalene-2,7-disulfonic acid) has the following structure:

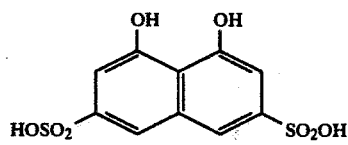

Chromotropic acid is preferably used in salt form. The disodium salt of 4,5-dihydroxynaphthalene-2,7-disulfonic acid dihydrate is especially preferred.

Preferred amidobetaines are the carboxy- and sulfobetaines marketed under the trademark LONZAINE ® C and LONZAINE ® CS, respectively, by the Swiss firm Lonza.

The preferred betaines have the following structure:

LONZAINE ® C:

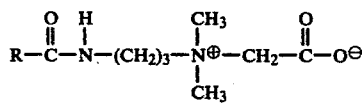

-continued
LONZAINE® CS:

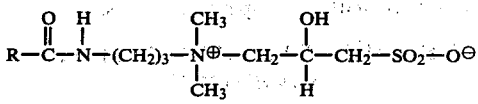

wherein R represents a straight chain coconut oil residue having between about 10 and 14 carbon atoms in the chain.

LONZAINE® C and CS are commercially available as solutions containing 30% and 50% active ingredient, respectively, at pH ranges of about 4.5–5.5 and 7.0–8.5, respectively.

In the practice of the invention, a urea-containing liquid sample is mixed with a working reagent comprising an acidic solution of o-phthalaldehyde, chromotropic acid or a salt thereof, and the amidobetaine. The reagent preferably contains sulfuric acid. Only about 2 mL of working reagent is required for each 10 μL of sample in the end point procedure and 2 mL of working reagent for each 50 μL of sample in the kinetic procedure.

The working reagent is preferably prepared by mixing a first aqueous reagent solution comprising o-phthalaldehyde and sulfuric acid with a second aqueous reagent solution comprising chromotropic acid (or a salt thereof), the amidobetaine, and sulfuric acid.

If desired, a small amount of ethylene glycol can be included in the chromotropic acid solution to enhance stability.

Upon mixing of the urea-containing liquid sample with the working reagent, the o-phthalaldehyde and urea react to form the isoindoline derivative intermediate, as described above, which in turn reacts with the chromotropic acid component to produce an intensely colored reaction product which is linearly related to the urea concentration in the sample, and which follows Beer's law over a wide range of urea concentrations. The concentration of the colored substance is readily determinable by standard spectrophotometric techniques.

The presence of the amidobetaine enhances precision, prevents protein precipitation, enhances the flow properties of the reagent system, and eliminates the need for an empirical conversion factor between serum absorbance and urea concentration when an aqueous calibrator is used.

The color-forming reaction is conveniently carried out at between about 25° C. and 37° C., preferably at 37° C. The method and reagent of the invention is suitable for end point, continuous flow, and kinetic urea measurement. Due to the presence of the amidobetaine and the properties imparted by the sulfonic acid groups of chromotropic acid, the reagent of the invention is particularly suitable for use in analytical systems having flow-through cuvettes. The reagent tends to maintain the cleanliness of the cuvettes, and will not attach to polymeric cuvette materials, even after long exposure.

The reagent is suitable for use in virtually any colorimetric instrument having programmable incubation facilities, or in equipment having constant temperature equipment, such as a constant temperature bath or block.

It has been found that, in the practice of the invention, maximum absorbance occurs at between about 445–455 nm at 37° C. The color-forming reaction in the end point procedure is rapid; after a reaction time of less than about 20 minutes, the colored reaction product follows Beer's law over the range of at least 0–80 mg urea nitrogen/dl. The total reaction time in the manual kinetic procedure need not exceed 2.5 minutes.

The invention is useful in the analysis of urea in any type of sample, including substantially colorless body fluids, such as urine, spinal fluid, blood serum and blood plasma, or in naturally colored body fluids such as whole blood, for example. To analyze naturally colored fluids, an absorbance reading should be taken immediately before the reaction starts, and 20 minutes after initiation of the reaction. The difference in absorbance readings corresponds to the concentration of the colored reaction product, as determined by comparison with an aqueous or serum calibrator.

The reagent of the invention is highly soluble in aqueous solutions under a wide variety of conditions. It is believed that solubility is enhanced by the presence of two sulfonic acid groups on the chromotropic acid molecule. Furthermore, the reagent's relatively high stability is believed to be a result of the presence of the two highly electrophilic sulfonic acid groups, which tend to offset the nucleophilic character of the hydroxy groups present in the chromotropic acid molecule.

Use of the reagent system of the invention enhances the precision of the well-known kinetic method of determination, as compared with the prior o-phthalaldehyde-chromotropic acid system of Gindler U.S. Pat. No. 4,273,556.

In the kinetic urea determination method, the reagents are mixed with a urea-containing liquid sample, and the absorbance of the reaction mixture at the end of a first time period (e.g. 30 seconds) and the absorbance at the end of a second time period (e.g. 90 or 120 seconds) after mixing are taken. The difference between these absorbances is then compared directly with a calibration graph obtained using aqueous calibrator solutions. No empirical conversion factor between serum and aqueous calibrator absorbances is required. In the manual kinetic procedure, a 60-second delay is used at room temperature following the mixing of 50 μL of sample and 2.00 mL working reagent before following the color development over 90 to 120 minutes at 37° C.

Both of the specific amidobetaines disclosed herein provide improved results over the system of Gindler Pat. No. 4,273,556, but the sulfoamidobetaine (e.g. LONZAINE® CS) has proven to be more sensitive than the carboxyamidobetaine (LONZAINE® C).

The ratios of reagents described in the Examples, below, may be varied, but the reaction rate decreases with decreasing o-phthalaldehyde concentrations. Also, the ratios of stock reagents may be varied.

The amidobetaines effectively prevent protein precipitation, and may be used as the only surfactant in the system.

The reagents of the invention are adequately stable in aqueous acidic solutions. The chromotropic acid component may be packaged in an aqueous acid solution, which preferably includes the amidobetaine, for addition to separately packaged o-phthalaldehyde solution to form the working reagent. Thus, only two solutions are required.

The working reagent is adequately stable, and need not be prepared immediately before use, but may be stored for a period of at least several days at room temperature.

It is believed that the working reagent of the invention is of low toxicity due to the presence of two sulfonic acid groups on the chromotropic acid molecule, which make the molecule unlikely to cross cell membranes.

As a hindered molecule, chromotropic acid experiences relatively little, if any interference from common drugs such as sulfa drugs and sulfonyl ureas, which are widely used antidiabetic drugs.

EXAMPLES

The use of the method and reagents of the invention is illustrated by reference to the following detailed examples. It should be understood, however, that the invention is not to be limited to the details of the examples, which are intended to be illustrative only.

EXAMPLE 1

Preparation of Working Reagent of the Invention

A. O-phthalaldehyde Reagent Solution

An o-phthalaldehyde solution is prepared by mixing 2.08 gm o-phthalaldehyde and 85.33 mL concentrated (18 M) sulfuric acid. The solution volume is brought to 1 liter by addition of deionized water.

B. Chromogenic Compound Solution I

A quantity of deionized water is mixed with 48.0 gm of 4,5-dihydroxynaphthalene-2,7-disulfonic acid disodium salt, dihydrate (98%), 540 mL LONZAINE® CS, 280 mL ethylene glycol, and 2.5 mL concentrated (18 M) sulfuric acid. The use of ethylene glycol is optional, and enhances stability.

The solution volume is brought to 1 liter by addition of deionized water.

C. Chromogenic Compound Solution II

A quantity of deionized water is mixed with 48 gm of 4,5-dihydroxynaphthalene-2,7-disulfonic acid disodium salt, dihydrate (98%), 748 ml LONZAINE® C, and 4.0 ml concentrated (18 M) sulfuric acid.

The solution volume is brought to 1 liter by addition of deionized water.

D. Working Reagent

Two working reagents are prepared by mixing 15 volumes of the o-phthalaldehyde reagent solution (Example 1(A)) with 1 volume of either of the chromogenic compound solutions I or II (Examples 2(B) and 2(C)), after filtering each of the solutions through Whatman No. 54 filter paper. The working reagents are referred to herein as working reagents I and II, respectively.

EXAMPLE 2

Preparation of Reference Working Reagent (U.S. Patent No. 4,273,556)

A. O-phthalaldehyde Reagent Solution

An o-phthalaldehyde solution is prepared by mixing 3.90 gm o-phthalaldehyde and 160 mL concentrated (18 M) sulfuric acid. The solution volume is brought to 1 liter by addition of deionized water.

B. Chromogenic Compound Solution

A quantity of deionized water is mixed with the following:

8.5 gm—4,5-dihydroxynaphthalene-2,7-disulfonic acid (Aldrich, disodium salt, dihydrate, 98%)
50 mL—ethylene glycol
8.5 mL—concentrated sulfuric acid (18 M)
25 gm—Armak ETHOMEEN® C/25
22.5 gm—BASF Wyandotte PLURONIC® 25R8
34 gm—BASF Wyandotte TETRONIC® 707
25 gm—boric acid The solution volume is brought to 1 liter by addition of deionized water.

ETHOMEEN® C/25 comprises cocoamine having 15 ethylene oxide units per molecule, and effectively prevents protein precipitation. The use of PLURONIC® 25R8 and TETRONIC® 707 eliminates turbidity.

C. Working Reagent

Equal volumes of the o-phthalaldehyde solution (Example 2(A)) and chromogenic compound solution (Example 2(B)) are mixed after filtration of each solution through Whatman No. 54 filter paper.

EXAMPLE 3

Kinetic Urea Determination Using Reference Working Reagent (U.S. Pat. No. 4,273,556)

Kinetic urea nitrogen determination was carried out on a series of samples of human sera, using the following procedure:

2.00 mL of the reagent of Example 2(C) was added to 50 μL of each sample. Each sample was incubated for 60 seconds at room temperature and placed in a Gilford Stasar III thermocuvet at 36.94° C. and the absorbance at 450 nm was recorded at intervals of 30 seconds and 120 seconds.

Each sample had previously been analyzed for urea nitrogen concentration by the SMAC® multiple Auto Analyzer® method, to provide "given" urea nitrogen values (mg/dL). "Found" urea nitrogen values, F, were calculated by direct comparison of the differences in absorbance between 120 and 30 seconds with an aqueous calibrator.

The "found" values were uniformly lower than the given values. Therefore, the use of an empirical conversion factor, as follows, was necessary.

The serum urea nitrogen concentration was found to be equal to 44 W/D (mg/dL) where W equals the absorbance change for serum between 30 and 120 seconds and D equals the absorbance change for a 40 mg/dL aqueous calibrator between 30 and 120 seconds. In this case, $D = 0.2605$ and $44/D = 168.8$.

After carrying out the foregoing analysis on 50 serum specimens, a least squares analysis indicated that, with the use of the empirical conversion factor given above, the correlation coefficient between given values and values found using the empirical conversion factor was 0.9986.

EXAMPLE 4

Kinetic Urea Determination Using Working Reagents I and II of Example 1

Kinetic urea determination was performed on two series of human sera using working reagents I and II of Example 1(D), and following the procedure of Example 3, except that differential absorbance readings were taken at 30 and 90 seconds, rather than at 30 and 120 seconds.

It was found in each case that the "found" urea nitrogen values F corresponded with the "given" values G determined independently by SMAC® analysis, and that no empirical conversion factor between serum absorbance and serum urea nitrogen concentration was necessary.

In each case, statistical analyses (Student-t Test, Wilcoxon Signed Rank Test, Sign Test) indicated that an upward bias of about 1 mg/dL existed between the method of the invention and the "given" (SMAC®) values. No significant difference between the ([Found Value]—1 mg urea nitrogen/dL) and the corresponding given values existed.

The correlation coefficient between given values and found values (without the use of an empirical conversion factor) was 0.997.

The foregoing detailed description is given for clearness of understanding only and no unnecessary limitations are to be understood therefrom, as modifications will be obvious to those skilled in the art.

We claim:

1. A method of demonstrating the presence of urea in a liquid sample, said method comprising the step of mixing said sample with a reagent comprising o-phthalaldehyde, a chromogenic compound selected from the group consisting of chromotropic acid and its salts, and a long hydrocarbon chain amidobetaine to produce a colored reaction product.

2. The method of claim 1 wherein said betaine is a sulfo- or carboxy-betaine.

3. The method of claim 2 wherein said betaine has either of the following structures:

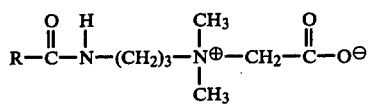

or

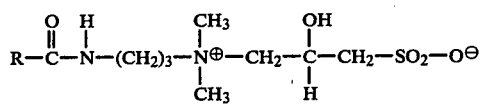

where R is a straight chain coconut oil residue having between about 10 and 14 carbon atoms in said chain.

4. A method of demonstrating the presence of urea in a sample of a human body fluid comprising the step of mixing said sample with o-phthalaldehyde and a chromogenic compound selected from the group consisting of chromotropic acid and its salts, under slightly acidic conditions in the presence of an amidobetaine having either of the following structures:

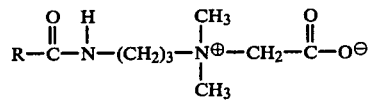

or

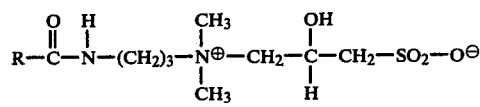

where R is a straight chain coconut oil residue having between about 10 and 14 carbon atoms in said chain, to produce a colored reaction product.

5. A method of determining the urea concentration is a liquid sample comprising the steps of:
   (a) adding o-phthalaldehyde, a chromogenic compound selected from the group consisting of chromotropic acid and its salts, and a long hydrocarbon chain amidobetaine to said liquid sample;
   (b) maintaining said sample at a temperature at which said chromogenic compound, said o-phthalaldehyde and said urea in said sample react to produce a colored reaction product;
   (c) obtaining a colorimetric absorbance reading for said sample; and
   (d) comparing said absorbance reading with calibration means.

6. The method of claim 5 wherein said chromogenic compound comprises chromotropic acid.

7. The method of claim 5 wherein said chromogenic compound comprises the disodium salt of chromotropic acid.

8. The method of claim 5 wherein said amidobetaine has either of the following structures:

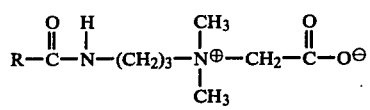

or

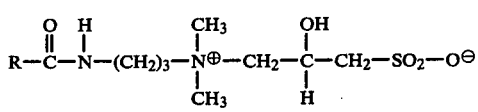

where R is a straight chain coconut oil residue having between about 10 and 14 carbon atoms in said chain.

9. In a method of determining the urea concentration in a liquid sample comprising the steps of mixing said sample with o-phthalaldehyde and a chromogenic compound selected from the group consisting of chromotropic acid and its salts under slightly acidic conditions to form a colored reaction product, obtaining a colorimetric absorbance reading of said sample and comparing said absorbance reading with calibration means, the improvement wherein said colored reaction product is formed in the presence of a long hydrocarbon chain amidobetaine.

10. The method of claim 9 wherein said amidobetaine has either of the following structures:

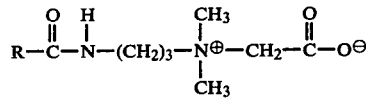

or

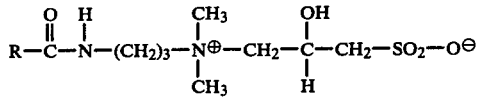

where R is a straight chain coconut oil residue having between about 10 and 14 carbon atoms in said chain.

11. A method of determining the urea concentration of a liquid sample, said method comprising the steps of:
   (a) adding said sample to a sample container;

(b) adding equal amounts of a reagent comprising a solution of o-phthalaldehyde, a chromogenic compound selected from the group consisting of chromotropic acid and its salts, and a long hydrocarbon chain amidobetaine to said sample container and a blank container;

(c) maintaining the contents of each said container at a temperature at which said o-phthalaldehyde and said urea in said sample react to produce a colored reaction product;

(d) obtaining first colorimetric absorbance readings for each of said blank and sample containers at the end of a first time period;

(e) obtaining second colorimetric absorbance readings for each of said blank and sample containers at the end of a second time period;

(f) computing the difference between said first and second absorbance readings for each of said sample and blank containers; and, (g) comparing said differences with calibration means.

12. The method of claim 11 wherein said amidobetaine is selected from the group consisting of betaines having the following structures:

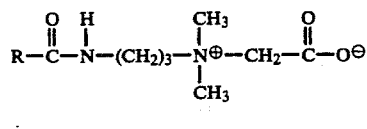

or

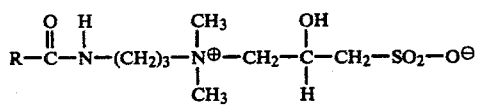

where R is a straight chain coconut oil residue having between about 10 and 14 carbon atoms in said chain.

13. A reagent for colorimetric urea determination consisting essentially of a solution of (a) o-phthalaldehyde, (b) a chromogenic compound selected from the group consisting of chromotropic acid and its salts, and (c) a long hydrocarbon chain amidobetaine.

14. A reagent for colorimetric urea determination consisting essentially of an acidic solution of (a) o-phthalaldehyde, (b) a chromogenic compound selected from the group consisting of chromotropic acid and its salts, and (c) a long hydrocarbon chain amidobetaine selected from the group consisting of compounds of the formula

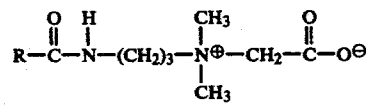

or

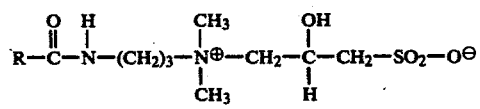

where R is a straight chain coconut oil residue having between about 10 and 14 carbon atoms in said chain.

15. A reagent kit for colorimetric determination of urea, said reagent kit consisting of a package containing a first container containing a first solution comprising a colorimetric amount of a chromogen selected from the group consisting of chromotropic acid and its salts, and a second container containing a second solution comprising a colorimetric amount of o-phthalaldehyde, one of said first and second solutions further comprising a long hydrocarbon chain amidobetaine.

16. The reagent kit of claim 15 wherein said amidobetaine is selected from the group consisting of compounds of the formula

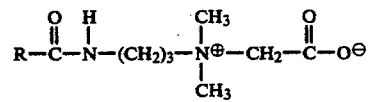

or

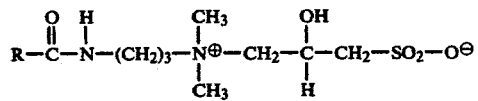

where R is a straight chain coconut oil residue having between about 10 and 14 carbon atoms in said chain.

* * * * *

UNITED STATES PATENT AND TRADEMARK OFFICE
CERTIFICATE OF CORRECTION

PATENT NO. : 4,357,144
DATED : Nov. 2, 1982
INVENTOR(S) : E. Melvin Gindler and Olga Daskalakis It is certified that error appears in the above-identified patent and that said Letters Patent are hereby corrected as shown below:

Column 3, line 58, delete "attach to" and insert --attack-- in lieu thereof; and Claim 11, line 8 before "o-phthalaldehyde" insert --chromogenic compound, said".

Signed and Sealed this

Twelfth Day of April 1983

[SEAL]

Attest:

GERALD J. MOSSINGHOFF

Attesting Officer    Commissioner of Patents and Trademarks